United States Patent
Blinman et al.

(10) Patent No.: US 10,117,674 B2
(45) Date of Patent: Nov. 6, 2018

(54) CANNULA ANCHOR

(75) Inventors: Thane Blinman, Philadelphia, PA (US); Michael Patton, Austin, TX (US); Harrith Hasson, Albuquerque, NM (US)

(73) Assignee: Stryker Corporation, San Jose, CA (US)

( * ) Notice: Subject to any disclaimer, the term of this patent is extended or adjusted under 35 U.S.C. 154(b) by 758 days.

(21) Appl. No.: 12/605,199

(22) Filed: Oct. 23, 2009

(65) Prior Publication Data

US 2011/0028796 A1 Feb. 3, 2011

Related U.S. Application Data

(60) Provisional application No. 61/107,870, filed on Oct. 23, 2008.

(51) Int. Cl.
| | |
|---|---|
| *A61M 31/00* | (2006.01) |
| *A61M 37/00* | (2006.01) |
| *A61B 17/34* | (2006.01) |
| *A61B 17/06* | (2006.01) |

(52) U.S. Cl.
CPC ...... *A61B 17/3423* (2013.01); *A61B 17/3421* (2013.01); *A61B 17/06061* (2013.01); *A61B 2017/349* (2013.01); *A61B 2017/3492* (2013.01)

(58) Field of Classification Search
CPC ......... A61B 17/06061; A61B 17/3421; A61B 17/3423; A61B 2017/349; A61B 2017/3492
USPC ...................................... 604/93.01
See application file for complete search history.

(56) References Cited

U.S. PATENT DOCUMENTS

| | | | | |
|---|---|---|---|---|
| 5,836,913 | A * | 11/1998 | Orth et al. | ..................... 604/107 |
| 6,638,265 | B1 * | 10/2003 | Ternamian | ......... A61B 17/3421 604/523 |
| 2006/0217665 | A1 * | 9/2006 | Prosek | ............... A61B 17/3421 604/167.02 |
| 2007/0156117 | A1 * | 7/2007 | Adams et al. | ................. 604/533 |

FOREIGN PATENT DOCUMENTS

WO    WO 2006133066 A2 * 12/2006    ......... A61F 9/00772

\* cited by examiner

*Primary Examiner* — Jason Flick
(74) *Attorney, Agent, or Firm* — DuBois, Bryant & Campbell, LLP; William D. Wiese

(57) ABSTRACT

Cannula anchor assemblies are disclosed which consist of a threaded cannula and a cannula anchor. The cannula anchor system allows for secure anchoring into the body wall, and proper cannula height adjustment prior to and during surgery. Sutures through the body wall may be secured to the cannula anchor either directly through the cannula anchor, or around suture posts attached therein. The cannula anchor also prevents excessive plunge of a trocar into the patient. The cannula anchor is generally configured with internal threads that mate with a threaded cannula.

5 Claims, 6 Drawing Sheets

CANNULA ANCHOR

PRIORITY STATEMENT UNDER 35 U.S.C. § 119 & 37 C.F.R. § 1.78

This non-provisional application claims priority based upon prior U.S. Provisional Patent Application Ser. No. 61/107,870 filed Oct. 23, 2008 in the name of Michael T. Patton, Richard Mazzolla, Harrith Hasson, and Thane Blinman, entitled "Cannula With Adjustable Anchor," the disclosure of which is incorporated herein by reference.

BACKGROUND OF THE INVENTION

Laparoscopy is a minimally invasive surgical procedure that utilizes a small tubular camera (laparoscope) to view abdominal and pelvic organs. During laparoscopy, devices called "trocars" are used to puncture the abdominal wall and provide access channels for the camera and thin laparoscopic surgical instruments. Since smaller incisions are made during these procedures, there is less patient trauma and reduced hospitalization. As a result, laparoscopy continues to grow in popularity.

A trocar assembly generally includes two major components, an obturator and a cannula. The obturator typically includes an elongate body having a sharpened distal tip. The sharp distal tip pierces and cuts the tissue forming the body wall. The cannula generally has a cylindrical configuration and a seal-valve housing. As the trocar is pushed or otherwise moved through the body wall, the sharp distal tip of the obturator functions to cut the tissue and provide an opening for the trocar. Once the trocar is operatively positioned, the obturator can be removed leaving the cannula to provide working access into the body cavity. For example, a laparoscope may be inserted through the cannula to view the body cavity or surgical instruments may be inserted through the cannula to perform ligations or other procedures.

The use of cannulas in laparoscopic surgery is well known. Once initial access to the abdominal cavity is attained, it is filled with carbon dioxide gas to allow for optimal viewing with the laparoscope and room for instrument manipulation. The cannula, which maintains the incision open to receive surgical instruments, must have a sealing mechanism that prevents or limits the escape of the gas when instruments of various diameters are inside. A valve mechanism prevents the escape of gas when instruments are removed from the cannula.

During the surgical procedure, it is desirable to secure or anchor the cannula position inside the incision (e.g., fascia) or in the skin to prevent movement of the cannula relative to the abdominal wall, and to prevent the cannula from slipping out of the incision, causing loss of insufflation pressure from the abdominal cavity. The present invention provides a novel cannula anchor assembly that overcomes deficiencies currently known in the art.

SUMMARY OF THE INVENTION

The present invention provides an improved cannula and, more specifically, a cannula anchor system with cannula threads in combination with an internally threaded cannula anchor for use in a wide variety of surgical procedures and is intended to easily secure laparoscopic cannulas in the body wall to prevent accidental cannula slippage. It is generally directed towards a cannula that prevents a surgeon from having to re-insert the cannula one or more times during the surgical procedure. While the cannula anchor system of the present invention is described herein for use with a surgical trocar, it is also well suited for a variety of other uses in which one apparatus is inserted and removed through an opening.

In one embodiment, the cannula anchor system consists of a threaded cannula and a single cannula anchor. The cannula anchor has internal threads, and its position on the cannula may be adjusted by rotating the cannula clockwise or counterclockwise. A suture can be threaded through the cannula anchor directly into body tissue to secure the cannula anchor system into place.

In an alternative embodiment, the cannula anchor can be constructed out of multiple materials to maximize its ability to be threaded up and down, and to be secured to the body tissue.

The foregoing has outlined rather broadly certain aspects of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DESCRIPTION OF THE DRAWINGS

A better understanding of the system and method of the present invention may be had by reference to the drawing figures, wherein.

DESCRIPTION OF THE PREFERRED EMBODIMENTS

The present invention is an improved cannula anchor system to secure a cannula in the body wall during laparoscopic surgery. It should be appreciated that the present invention is equally applicable to any appropriate surgical procedure. References to surgical procedures and other terms used herein may be applicable to medical and veterinary surgery as well as other non-medical applications.

Figure 1:
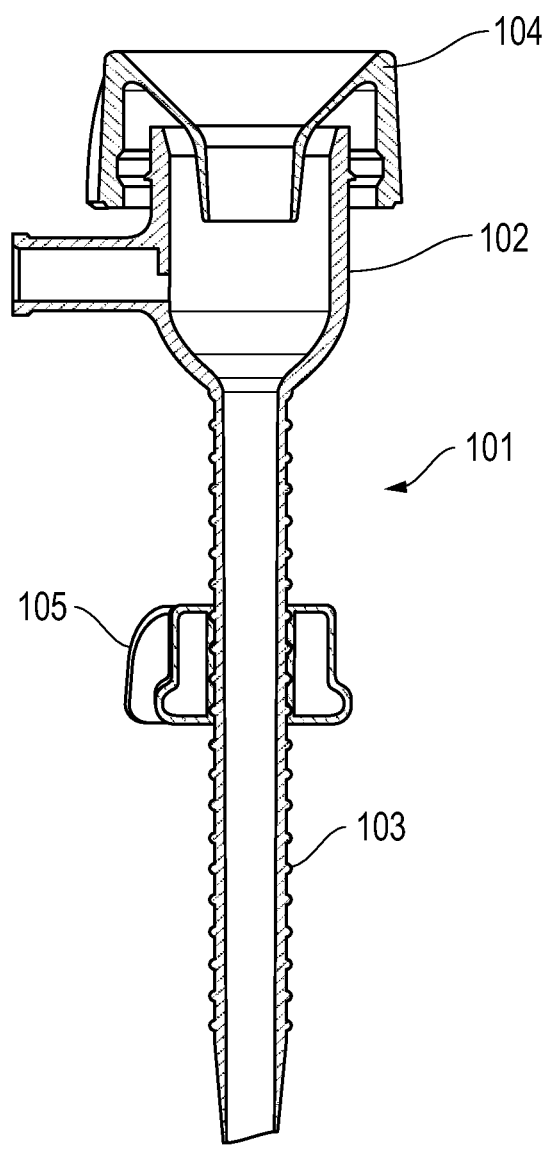
FIG. 1 is a cross-sectional view of one embodiment of a cannula anchor system, illustrating a threaded cannula with a cannula anchor attached.
Figure 2:
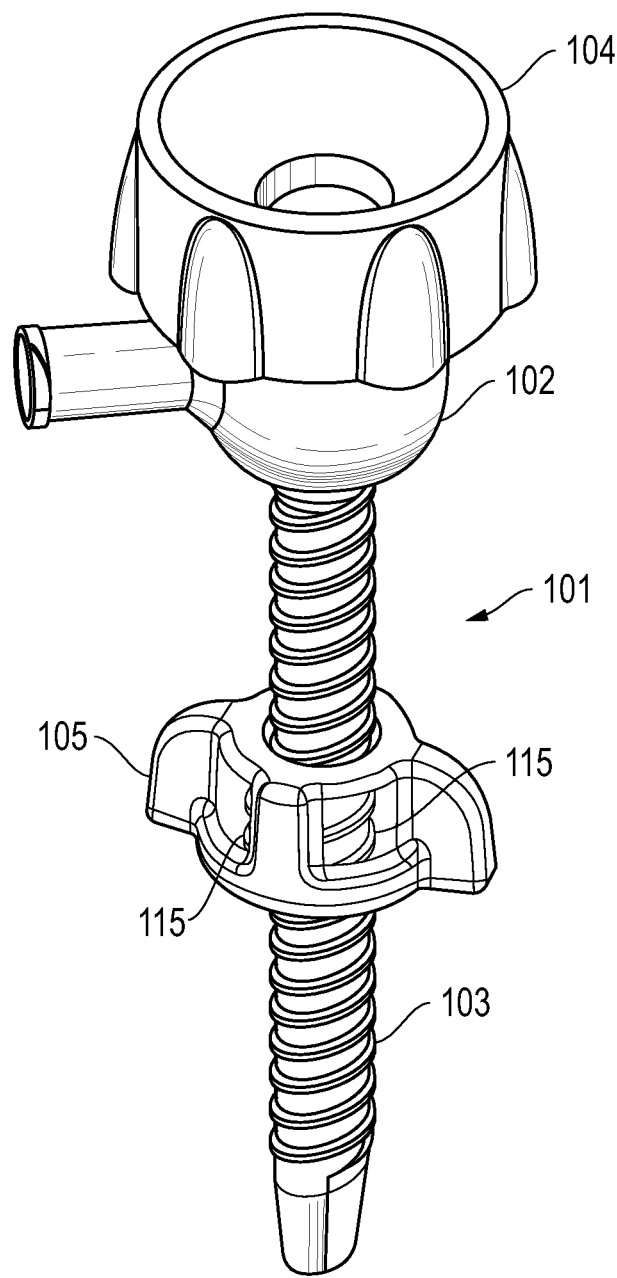
FIG. 2 is an isometric view of one embodiment of the cannula anchor system.

Referring now to the various figures of the drawing wherein like reference characters refer to like parts throughout the several views. FIG. 1 and FIG. 2 illustrate a cannula 101 in accordance with one preferred embodiment of the present invention. The cannula 101 is comprised of a cannula body 102, which houses the seal and valve, threaded cannula 103, and cannula cap 104. A cannula anchor 105 is shown assembled on the cannula threads 103. The height of the cannula 101 can be adjusted by rotating the cannula 101 clockwise and counterclockwise, while holding the cannula anchor 105 steady. The cannula threads 103 mate with the internal threads on the cannula anchor 105. The threads can be constructed in a clockwise or counterclockwise manner. The cannula anchor 105 may be secured into the body wall by suturing directly through the cannula anchor into the body wall. Alternatively, cannula anchor 105 may be constructed with one or more windows 115 where sutures may be tied off. The cannula anchor 101 may be made of a variety of materials, including polymers, plastics, and metal. The cannula anchor 101 can also be used as a barrier to prevent excessive plunge of the trocar into the body cavity during insertion, or during instrument insertion through the cannula throughout the procedure.

Figure 3:
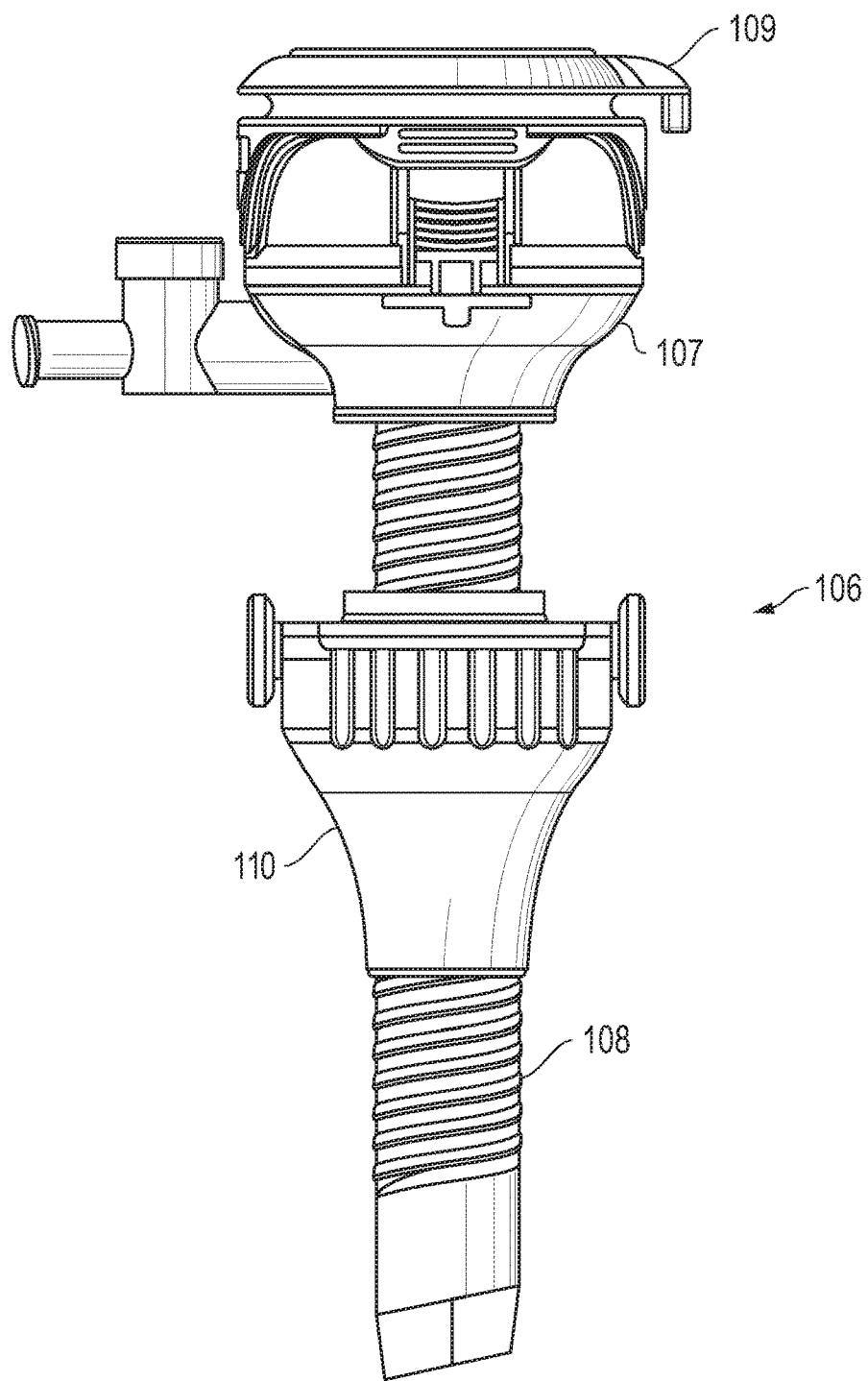
FIG. 3 shows another embodiment of the cannula anchor system.

FIG. 3 shows another embodiment of a cannula anchor system, illustrating a cannula 106 in combination with a cannula anchor 110. In this embodiment, cannula 106 is comprised of cannula body 107, cannula threads 108, and cannula cap 109.

Figure 4:
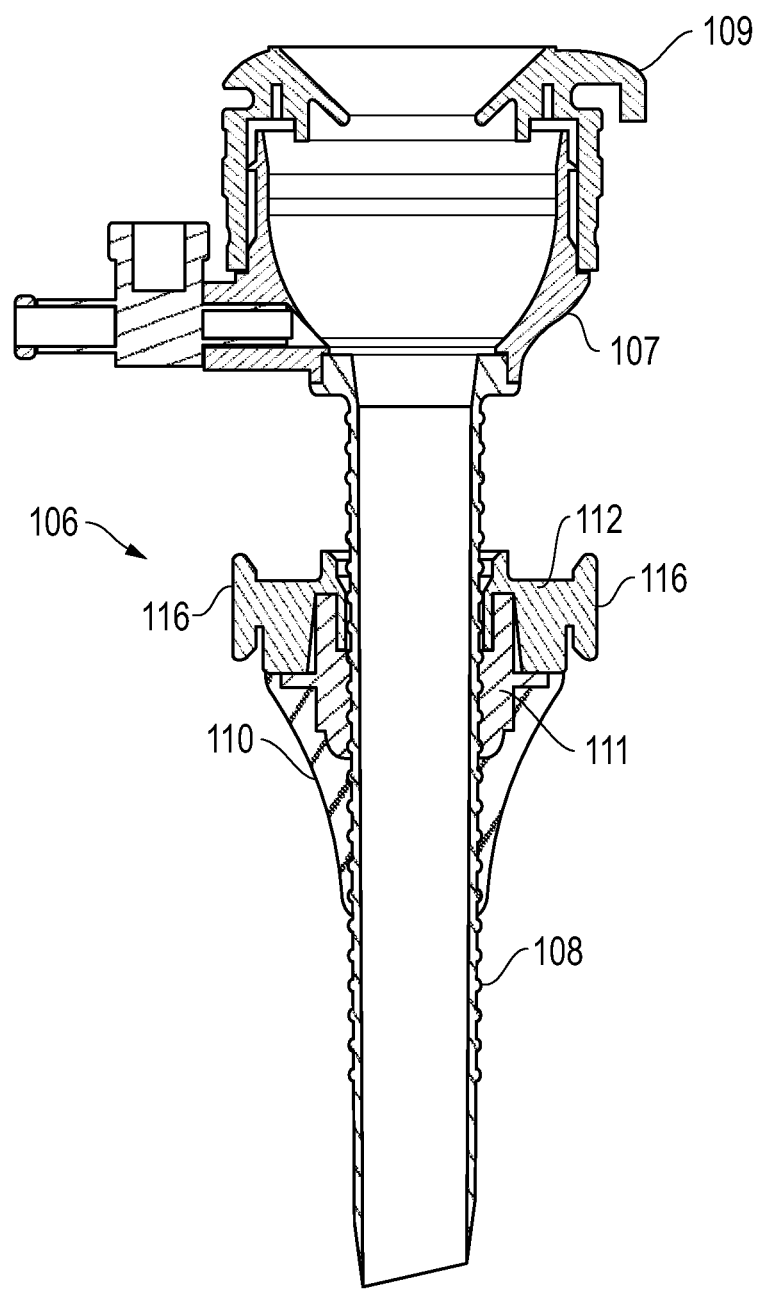
FIG. 4 shows a cross-sectional view of another embodiment of the cannula anchor system.

FIG. 4 shows a cross-sectional view of the cannula anchor system illustrated in FIG. 3. Cannula anchor 110 is shown comprised of two components, threaded cannula insert 111 and suture cone 112. In this embodiment, the height of the cannula 106 can be adjusted by rotating the cannula 106 clockwise and counterclockwise, while holding the cannula anchor 110 steady. This embodiment provides the means to wrap suture around suture posts 116 as opposed to suturing directly through the cannula anchor material, when securing the cannula anchor system to the body.

Figure 5A:
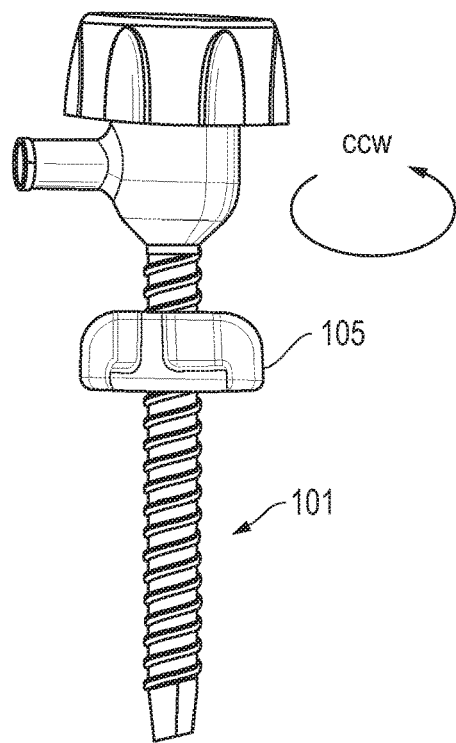
FIG. 5A illustrates one embodiment of the cannula anchor system with the cannula anchor on the proximal portion of the cannula.
Figure 5B:
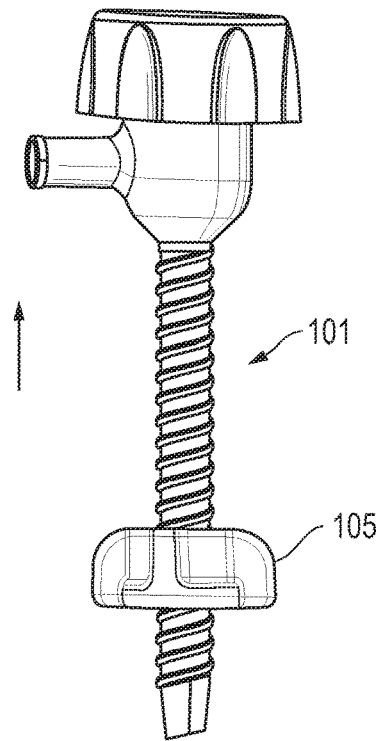
FIG. 5B illustrates one embodiment of the cannula anchor system with the cannula anchor on the distal portion of the cannula.

FIG. 5A shows the cannula anchor 105 in a proximal position on the cannula 101. This position allows more of the cannula 101 to extend into the body. If less room is required inside the body cavity, cannula 101 can be rotated counterclockwise, thus moving the cannula anchor 105 to a more distal position on the cannula 101.

Figure 6:
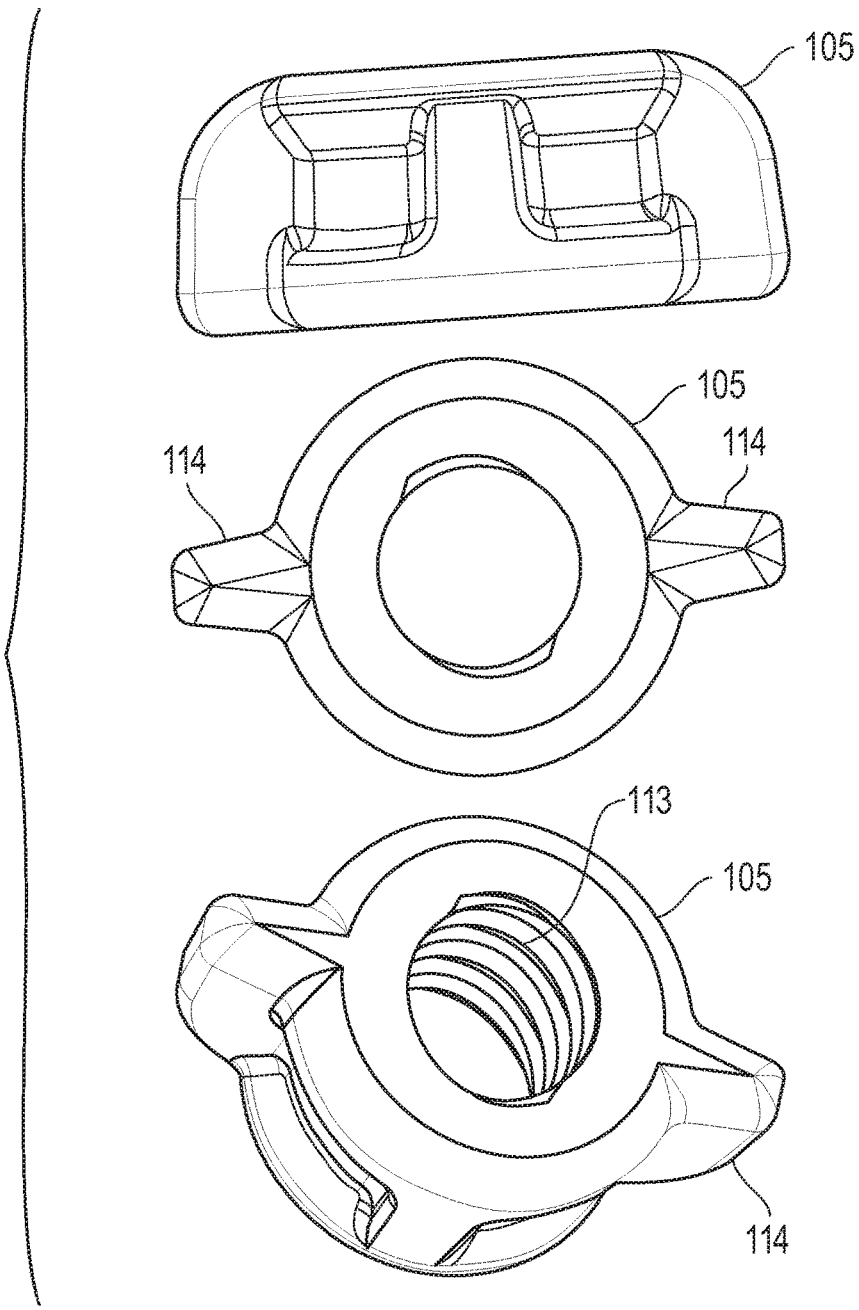
FIG. 6 illustrates three views of one embodiment of the cannula anchor.

FIG. 6 illustrates three views of the cannula anchor 105. The cannula anchor internal threads 113 are illustrated in the isometric view. Finger grips 114 may be added to the cannula anchor to provide the surgeon more leverage when adjusting the height of the cannula.

While the present system and method has been disclosed according to the preferred embodiment of the invention, those of ordinary skill in the art will understand that other embodiments have also been enabled. Even though the foregoing discussion has focused on particular embodiments, it is understood that other configurations are contemplated. In particular, even though the expressions "in one embodiment" or "in another embodiment" are used herein, these phrases are meant to generally reference embodiment possibilities and are not intended to limit the invention to those particular embodiment configurations. These terms may reference the same or different embodiments, and unless indicated otherwise, are combinable into aggregate embodiments. The terms "a", "an" and "the" mean "one or more" unless expressly specified otherwise. The term "connected" means "communicatively connected" unless otherwise defined.

When a single embodiment is described herein, it will be readily apparent that more than one embodiment may be used in place of a single embodiment. Similarly, where more than one embodiment is described herein, it will be readily apparent that a single embodiment may be substituted for that one device.

In light of the wide variety of possible seals available, the detailed embodiments are intended to be illustrative only and should not be taken as limiting the scope of the invention. Rather, what is claimed as the invention is all such modifications as may come within the spirit and scope of the following claims and equivalents thereto.

None of the description in this specification should be read as implying that any particular element, step or function is an essential element which must be included in the claim scope. The scope of the patented subject matter is defined only by the allowed claims and their equivalents. Unless explicitly recited, other aspects of the present invention as described in this specification do not limit the scope of the claims.

What is claimed is:

1. A cannula anchor assembly comprising:
   an internally threaded cannula insert positioned on a threaded cannula, the cannula insert positioned partially inside a suture cone and partially inside a cannula anchor;
   wherein said suture cone includes one or more suture posts configured to wrap suture around.

2. The cannula anchor assembly of claim 1, wherein a height of said threaded cannula relative to said internally threaded cannula insert can be adjusted by rotating clockwise.

3. The cannula anchor assembly of claim 1, wherein a height of said threaded cannula relative to said internally threaded cannula insert can be adjusted by rotating counterclockwise.

4. The cannula anchor assembly of claim 1, wherein said suture cone is configured to be penetrable by a suture needle.

5. The cannula anchor assembly of claim 1, wherein said suture cone includes at least one finger grip.

* * * * *